United States Patent [19]
Busson et al.

[11] Patent Number: 6,027,635
[45] Date of Patent: Feb. 22, 2000

[54] CONTINUOUS PYROLYSIS AND DECOKING PROCESS FOR USE IN THE PRODUCTION OF ACETYLENE

[75] Inventors: Christian Busson, Charbonniere; Henri Delhomme, Sainte Foy les Lyon, both of France

[73] Assignee: Institute Francais du Petrole, Rueil-Malmaison Cedex, France

[21] Appl. No.: 08/773,781

[22] Filed: Dec. 26, 1996

[30] Foreign Application Priority Data

Dec. 27, 1995 [FR] France ................................ 95/15527

[51] Int. Cl.⁷ .............................. C10G 9/12; B01J 8/04
[52] U.S. Cl. .................. 208/48 R; 208/132; 585/950; 585/920; 422/198; 422/199; 422/200
[58] Field of Search .................... 208/48 R, 132; 585/950, 920; 422/198, 199, 200

[56] References Cited

U.S. PATENT DOCUMENTS

| | | | |
|---|---|---|---|
| 1,470,359 | 10/1923 | Greenstreet | 208/48 R |
| 3,536,776 | 10/1970 | Lo | 585/636 |
| 3,579,601 | 5/1971 | Kivlen | 585/652 |
| 3,641,190 | 2/1972 | Kivlen et al. | 260/683 |
| 4,376,694 | 3/1983 | Lohr et al. | 208/48 R |
| 4,780,196 | 10/1988 | Alagy et al. | 208/130 |
| 5,321,191 | 6/1994 | Alagy et al. | 585/648 |
| 5,365,005 | 11/1994 | Weill et al. | 585/500 |
| 5,496,524 | 3/1996 | Weill et al. | 422/199 |

FOREIGN PATENT DOCUMENTS

| | | |
|---|---|---|
| 0 143 486 | 6/1985 | European Pat. Off. . |
| 0 539 270 | 4/1993 | European Pat. Off. . |
| 0 542 597 | 5/1993 | European Pat. Off. . |
| 0 591 856 | 4/1994 | European Pat. Off. . |

*Primary Examiner*—Walter D. Griffin
*Assistant Examiner*—Nadine Preisch
*Attorney, Agent, or Firm*—Millen, White, Zelano & Branigan, P.C.

[57] ABSTRACT

A process for the pyrolysis of hydrocarbons in a reactor with at least two rows which are parallel to each other in which at least one row is supplied with a non hydrocarbon fluid containing steam to decoke the reaction zone at least in part. At least one other row is supplied with a gaseous mixture containing at least one hydrocarbon and water, to pyrolyze said mixture.

16 Claims, 1 Drawing Sheet

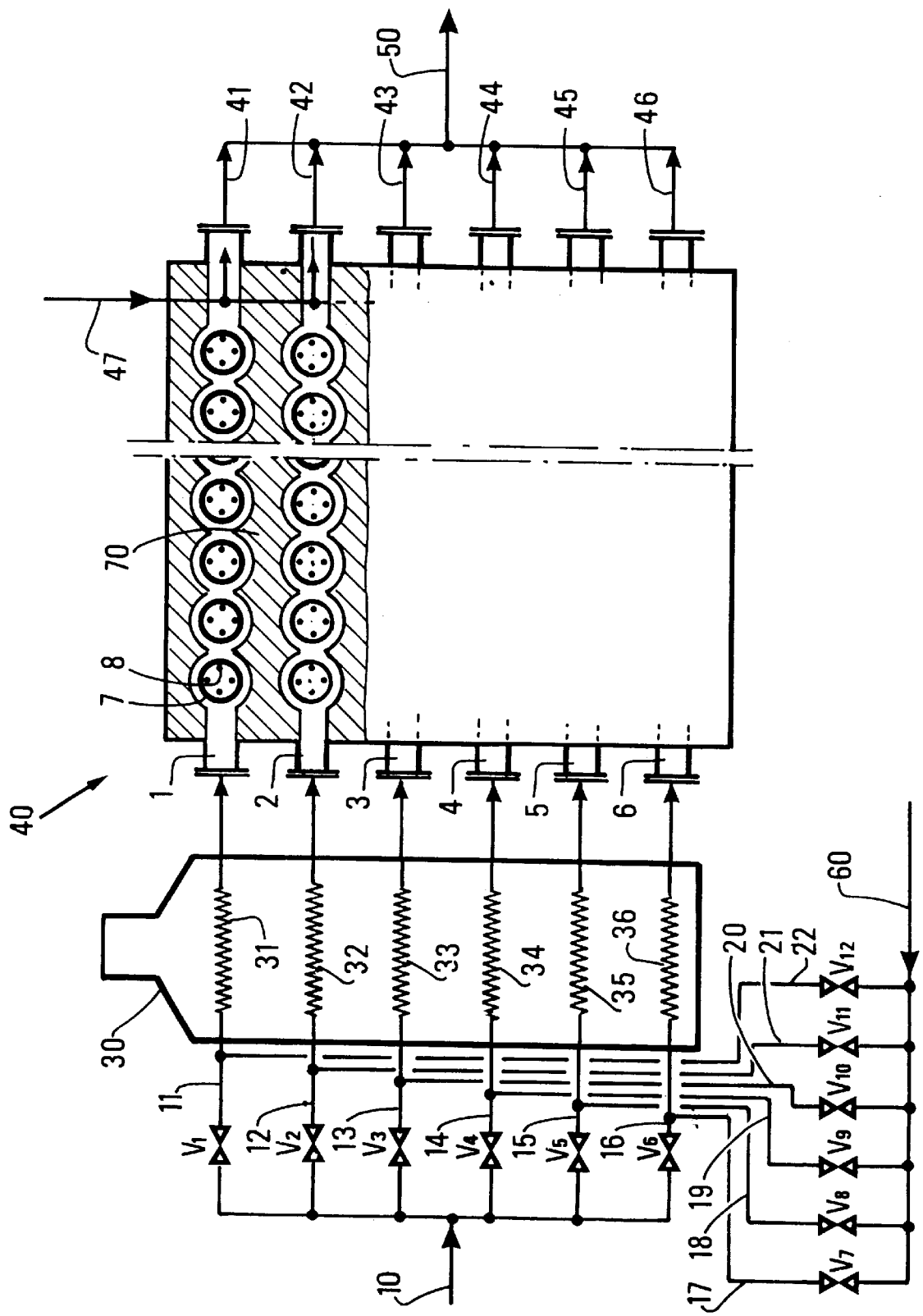

CONTINUOUS PYROLYSIS AND DECOKING PROCESS FOR USE IN THE PRODUCTION OF ACETYLENE

FIELD OF THE INVENTION

The invention concerns a process for the pyrolysis of a hydrocarbon feed containing at least one carbon atom which is carried out simultaneously with decoking of the coke deposited on the reactor walls.

It is of particular application to the continuous production of acetylene or acetylenic compounds such as methyl acetylene.

BACKGROUND OF THE INVENTION

The prior art is particularly illustrated in United States patents U.S. Pat. No. 3,641,190, U.S. Pat. No. 1,470,359, and European patents EP-A-0 591 856, EP-A-0 143 486, EP-A-0 542 597 and EP-A-0 539 270.

In processes for the high temperature thermal transformation of hydrocarbons containing at least one carbon atom, for example pyrolysis between 900° C. and 1500° C. or steam cracking at about 850° C. near the end of the heating zone, coke forms and deposits on the surface of the reactor walls. The reactor is then decoked, a process which is normally carried out in air at temperatures which are usually below 900° C., attempting in the case of metal furnaces to avoid any overheating or hot spots which could damage the metal tubes of the furnace. Exothermic decoking thus requires the whole unit to be shut down and in particular, it requires the furnace to be disconnected from the downstream heat exchangers, reducing the total productivity of the unit. Further, safety regulations require the hydrocarbon introduction lines to be disconnected and replaced by air introduction lines, thus requiring a very long downtime for the unit.

The same disadvantages are there when rebuilding the unit for the pyrolysis phase, with the additional necessity of purging the reaction zone and lines with an inert gas.

Pyrolysis of hydrocarbons containing at least one carbon atom to produce olefinic or acetylenic hydrocarbons has been described, in particular in our patent applications FR-A-2 715 583 and FR-A-2 732 014, which are hereby incorporated by reference.

Pyrolysis reactors of ceramic material have been used in which non impermeable walls which are advantageously of ceramic material determine channels in which the feed and the reaction effluents circulate. These walls advantageously have a shape which is adapted to create turbulence and which, for example, comprise cells or cavities about the heating means. These latter are generally sleeves containing an electric heating element or a gas burner.

SUMMARY OF THE INVENTION

One aim of the invention is to provide a process which can pyrolyse a hydrocarbon feed without stopping the unit to decoke the unit.

A further aim of the invention is to maintain the temperature of the facility at a relatively constant level during operation to avoid thermal stresses which would not be avoidable, in particular during use of a gas containing oxygen for the decoking step which is an exothermic reaction while the pyrolysis reaction is an endothermic reaction.

Because of the presence of non impermeable and therefore cheap walls in the reaction zone, we have noticed that it is possible to carry out a continuous pyrolysis process for a hydrocarbon feed and a reaction zone decoking process with no penalties.

In detail, the invention concerns a continuous pyrolysis and decoking process carried out in a reaction zone which is of refractory material, which is elongate in one direction (one axis), and which comprises a heating zone and a cooling zone following the heating zone, the heating zone comprising at least two rows which are substantially parallel to the axis separated by a wall, which is preferably non impermeable, of refractory material and located between two successive rows, at least one of said rows communicating with a gaseous mixture supply containing a hydrocarbon comprising at least one carbon atom and steam, at least one other of said rows communicating with a supply for a non hydrocarbon fluid comprising steam, said rows comprising heating means surrounded by sleeves which are substantially parallel to each other and substantially perpendicular to the reactor axis, wherein coke is deposited in the reaction zone, the process being characterized in that the gaseous mixture is circulated in at least one row of the heating zone to pyrolyse said mixture and to produce a temperature at the outlet to said zone of at least 850° C., and said fluid comprising steam is circulated in at least one other row of the heating zone to decoke the reaction zone at least in part and to produce a temperature at the outlet to said zone of at least 850° C., and in which hydrocarbons and a decoking effluent are recovered.

The invention is of particular application when the pyrolysis period before decoking is greater, preferably at least twice as long, as the decoking period.

The temperature in the row or rows in which pyrolysis is carried out is advantageously kept substantially equal to the temperature in the rows in which decoking is carried out.

Decoking the channels with very high temperature steam, at over 850° C. and preferably 1000° C. to 1400° C., produces sufficiently oxidising conditions at these temperatures to transform the coke and form carbon monoxide and hydrogen.

This is particularly advantageous when the ceramic reactors include non impermeable walls. Steam and hydrogen can then transfer through the wall of the row where decoking is occurring to the row in which pyrolysis takes place.

It has been observed that a transfer of hydrogen towards the pyrolysis row slows down deposition of coke thereon.

Further, a transfer of steam from the row in which decoking is taking place to the row in which pyrolysis takes place is not a problem since the pyrolysis reaction is carried out in the presence of steam. In the other direction, if hydrocarbons pass from the pyrolysis row to the row in which decoking is taking place, they find themselves in the presence of a great deal of water and are pyrolysed to the desired products.

The heating means may be electrical resistances contained in sleeves such as those described in the above patents or they may be constituted by sleeves containing a gas burner such as that described in our French patent application (FR-A-2 715 583).

Each row can comprise at least one layer of heating means, which layer is substantially parallel to the axis of the reaction zone, surrounded by sleeves which are substantially perpendicular to the axis.

We have observed that in the presence of electrical heating elements contained in relatively porous and cheap ceramic sleeves in which the impermeability is not perfect, a sleeve gas containing hydrogen and/or steam and/or an inert gas could be used and further, could diffuse from the inside to the outside of the sleeves without perturbing the pyrolysis reaction and without perturbing the decoking reaction.

The flow rate of the steam introduced into the decoking row can be 1.1 to 4 times greater than the flow rate of water introduced into the pyrolysis row. It is normally 2 to 3 times that used during pyrolysis.

In other words, during decoking, the hydrocarbon supply to the row to be decoked is cut and the flow rate of the water is increased so as not to provoke too much thermal perturbation in the gas pre-heating furnace upstream of the reaction zone.

In a first variation, the recovered hydrocarbons and the decoking effluent are mixed before being introduced into the cooling zone.

In a second variation, the recovered hydrocarbons and the decoking effluent are separately cooled in their respective rows, located in the cooling zone, then they may be mixed.

The cooling zone is usually a direct chilling zone which uses a cooling fluid, and is known to the skilled person.

In general, the flow rate of the water in the pyrolysis zone is such that the weight ratio of water/hydrocarbons is in the range 0.55 to 20, preferably in the range 0.65 to 10.

The pressure is generally in the range 1 to 15 bars absolute (0.1 to 15 MPa), preferably in the range 1 to 3 bars absolute, the weight ratio more particularly being in the range 0.8 to 5.

The pre-heated gases are introduced into the reactor at a temperature of about 400° C. to about 700° C., preferably 500° C. to 650° C.

Normally, the final temperature at the outlet to the pyrolysis zone is more than 850° C., more particularly in the range 1000° C. to 1400° C.

The characteristics of the heating elements, whether electrical or gas burners, their number, the distance separating them and their configuration have been described in the patents cited above.

This is also the case for the sleeves which protect them and isolate then from the fluids circulating in the reactor.

These same heating elements and these same sleeves with the same characteristics and configurations can be found in both the pyrolysis zone and in the zone (or row) in which steam decoking is carried out.

The invention also concerns an apparatus for carrying out the process.

More particularly, the pyrolysis and decoking unit comprises a pyrolysis reactor which is elongate in one direction (one axis) comprising at least two rows which are substantially parallel to the axis separated by a wall, which is preferably not impermeable, of refractory material located between two successive rows, each row comprising a plurality of heating means disposed in at least one layer of heating elements surrounded by sleeves of ceramic material which are substantially parallel to each other and substantially perpendicular to the reactor axis, at least one of the rows being connected to a feed supply line comprising at least one valve and to a steam supply line comprising at least one valve, at least one of said rows being connected to a supply line for a non hydrocarbon fluid containing steam and comprising at least one valve, said pyrolysis reactor comprising means for heat control and modulation connected to said heating means, the unit further comprising cooling means for the effluents produced in each row.

The unit has the advantage of being safe, reliable and easy to operate. It uses refractory materials, and more particularly ceramic materials known to the skilled person such as cordierite, mullite, silicon nitride or silicon carbide.

Non limiting examples of suitable hydrocarbon feeds are:

saturated aliphatic hydrocarbons such as methane, ethane, alkane mixtures (LPG), petroleum cuts such as naphthas, atmospheric gas oils and vacuum gas oils, the latter having an end boiling point of the order of 570° C.;

unsaturated hydrocarbons such as ethylene, propylene, butadiene, mixtures of alkanes and alkenes such as ethane+ethylene, and $C_3$, $C_4$ and $C_5$ steam cracking and catalytic cracking cuts.

On an industrial scale, steam cracking hydrocarbons are preferably used, namely ethane which can contain ethylene in highly variable but generally small amounts, and ethylene mixed with other hydrocarbons present in the steam cracking effluent.

BRIEF DESCRIPTION OF DRAWINGS

The invention will be better understood from the description of an embodiment, which is given purely by way of illustration and is in no way limiting, and which is given with reference to the accompanying FIGURE which shows a longitudinal cross section of a reactor on a plane which is parallel to the axis of the reactor.

DETAILED DESCRIPTION OF DRAWING

Hydrocarbon supply lines 11, 12, 13, 14, 15 and 16 controlled by valves V1, V2, V3, V4, V5 and V6 introduce the hydrocarbons into a pyrolysis and decoking reactor 40 via a line 10 mixed with water which is generally in the form of steam supplied via line 60. This line distributes the steam to lines 17, 18, 19. 20, 21 and 22 which are controlled by valves V7, V8, V9, V10, V11 and V12 respectively.

Valves V1 to V12 are adapted to allow circulation of a mixture of hydrocarbons and steam in a certain number of rows of the reactor, the pyrolysis rows, and to circulate steam alone in the other rows of the reactor, the decoking rows, to remove coke which deposits thereon during the pyrolysis reaction.

Lines 31, 32, 33, 34, 35 and 36 transport the hydrocarbon mixture and the water or transport water alone, and are respectively connected to lines 11 and 22, 12 and 21, 13 and 20, 14 and 19, 15 and 18 and finally, 16 and 17. These lines are pre-heated in pre-heating furnace 30 to a temperature of 400° C. to 700° C. and are connected to pyrolysis reactor 40.

As an example, since valve V1 closes line 11, line 31 receives only steam supplied via line 22 controlled by valve V12. In contrast, lines 32, 33, 34, 35 and 36 receive the mixture of hydrocarbons and water, all the other valves mentioned being open.

Reactor 40 is divided into longitudinal rows (1, 2, 3, 4, 5 and 6) which are substantially parallel to its axis. These rows are separated from each other by non impermeable walls which are of ceramic materials, the shape of which comprises cells adapted to encourage turbulence inside the row and thus to encourage the reaction. These rows contain sleeves of ceramic material 7 forming a layer which is substantially parallel to the reactor axis. These sleeves are substantially parallel to each other and substantially perpendicular to the reactor axis. They contain, for example, a plurality of electrical resistances 8 bathed in a sleeve gas which is selected from the group formed by steam, hydrogen, an inert gas and a mixture of two or more of these gases.

Steam line 31 is connected to row 1. Generally, the flow rate of the steam introduced into the row in which decoking is carried out is increased, for example to 2 to 3 times that used in the five other rows 2, 3, 4, 5 and 6 where pyrolysis takes place. These rows are thus connected to mixture lines 32, 33, 34, 35 and 36 respectively.

The terminal portion of the various rows of the reactors, intended for pyrolysis or decoking, receives pyrolysis or decoking effluents and each row is connected to a direct chilling line 47, comprising a controlled rate injector, for example for ethane if the feed is ethane, to cool the effluents. Once cooled to 800° C., for example, lines 41, 42, 43, 44, 45 and 46 which are connected to rows 1, 2, 3, 4, 5 and 6 respectively mix the various effluents which are evacuated via a line 50.

In a further embodiment, which is not illustrated, the effluents can be cooled by circulation through sealed conduits located in the terminal portion of the rows by indirect chilling then mixing as described above.

In a further embodiment which is not illustrated, the pyrolysis effluents and the decoking effluents from rows 1, 2, 3, 4, 5 and 6 are collected by lines 41, 42, 43, 44, 45 and 46 then mixed and sent to a direct or indirect quenching zone and, once cooled, evacuated via line 50.

Heating elements 8 are independently supplied with electrical energy by means of a pair of electrodes which are not shown in the FIGURE, pyrometric sensor thermocouples which are not illustrated are located in spaces in which the feed circulates and the temperature of each heating section can be automatically regulated using a conventional device for regulation and modulation which is not shown in the FIGURE, depending on the temperature profile selected. This applies both to the pyrolysis reaction and to that of decoking the sleeve walls.

EXAMPLE

A reactor as described in FIG. 1 was used to crack a mixture of ethane and steam to produce acetylene.

The reactor had 6 heating rows which were substantially parallel to its axis and separated by walls with cell-like walls of a ceramic material such as silicon carbide. Each row comprised a layer of electrical heating elements. The sleeves surrounding the electrical resistances were of silicon carbide and contained a sleeve gas, nitrogen.

Five rows operated in pyrolysis mode (nos. 1, 3, 4, 5 and 6) while a single row (no. 2) operated in decoking mode.

258 kg/h of ethane and 464 kg/h of steam were introduced into each pyrolysis row.

979 kg/h of steam was sent to row no. 2, operating in decoking mode, via valve V11. Hydrocarbon valve V2 was closed.

The mixture (ethane-water) to be pyrolysed and the decoking vapour were pre-heated to 630° C. and substantially linearly heated to 1200° C. in their respective rows at an absolute pressure of 1.3 bar.

The pyrolysis effluent was cooled to 800° C. at the pyrolysis reactor outlet by direct contact with 91 kg/h of ethane at 16° C. while the decoking effluent was cooled to 800° C. by direct contact with 85 kg/h of ethane at 16° C.

After 72 hours of pyrolysis in row no. 1, decoking thereof was commenced. The ethane flow was cut off by valve V1 and to avoid disturbing the thermal conditions in the preheater and the pyrolysis furnace, the steam flow rate (valve V12) was increased to 979 kg/h. Simultaneously, row no. 2 was supplied with 258 kg/h of ethane and 464 kg/h of water vapour by opening valve V2 and valve V11.

Decoking completion was indicated by the disappearance of carbon monoxide, which was analysed on-line by infrared, for example, at the pyrolysis furnace outlet.

Decoking was seen to be complete after 14 hours in each row where it was carried out, after which pyrolysis was immediately recommenced in the decoked row.

Thus five rows were in pyrolysis mode and one row was in decoking mode. 450 kg/h of acetylene was produced constantly and with no prolonged stoppages. The effluents from the six rows were mixed and sent via line 50 to product treatment and separation processes.

Clearly, depending on the decoking period for the selected feed, a reactor comprising 10 pyrolysis rows and 2 decoking rows which may be neighbouring or separated, could be used.

We claim:

1. A continuous pyrolysis and decoking process for producing an acetylenic compound comprising conducting the process in a reaction zone (40) of refractory material, said reaction zone being elongate in one direction (one axis), and comprising a heating zone and a cooling zone following the heating zone, the heating zone comprising at least two rows (1, 2) defining flow paths substantially parallel to the axis and separated by an outside wall (70) of refractory material located between two successive flow paths, said process comprising passing through at least one of said rows a gaseous mixture supply (10, 60) containing a hydrocarbon containing at least one carbon atom and steam, and passing through at least one other of said rows a supply (60) of a non hydrocarbon fluid comprising steam, said rows comprising heating means (8) surrounded by sleeves (7) located internally of said flow paths and substantially perpendicular to the reactor axis, wherein coke is deposited in the reaction zone, the process being characterized in that the gaseous mixture is circulated in at least one row of the heating zone to pyrolyze said mixture to form an acetylenic compound and to produce a temperature at the outlet to said zone of at least 850° C., and said non-hydrocarbon fluid comprising steam is passed into at least one other row of the heating zone in a sufficient quantity and at a sufficient temperature to decoke the reaction zone at least in part to form carbon monoxide and hydrogen endothermally and to produce a temperature at the outlet of said zone of at least 850° C., and a temperature in the zone sufficient for a later pyrolysis step and recovering hydrocarbons and a decoking effluent from said reaction zone, measuring the extent of decoking and when the reaction zone is sufficiently decoked, placing the reaction zone onstream as a heating zone for pyrolysis said process being conducted so that during the decoking, at least one pyrolysis zone is onstream so as to permit the gaseous mixture to be pyrolyzed continuously said mixture in the pyrolysis zone having a weight ratio of $H_2O$ to hydrocarbon of 0.55:1 to 20:1.

2. A process according to claim 1, wherein the temperature is substantially the same in each of the rows.

3. A process according to claim 1, in which the flow rate of the steam introduced into the decoking row is 1.1 to 4 times greater than a flow rate of steam introduced into a pyrolysis row.

4. A process according to claim 1, in which the recovered hydrocarbons and the decoking effluent are mixed before being introduced into the cooling zone.

5. A process according to claim 1, in which the recovered hydrocarbons and the decoking effluent are separately cooled in their respective rows in the cooling zone and may then be mixed.

6. A process according to claim 5, comprising directly cooling the recovered hydrocarbons and the decoking effluent with a cooling fluid.

7. A process according to claim 1, in which the sleeves contain at least one gas selected from the group consisting of hydrogen, steam and an inert gas.

8. A process according to claim 1, in which the gaseous mixture is circulated in at least one row of the heating zone to pyrolyse said mixture and produce a temperature at the outlet to said heating zone of about 1000° C. to 1400° C. and said fluid comprising steam is circulated in at least one other row of the heating zone to decoke the reaction zone at least partially, and to produce a temperature at the outlet to said heating zone of about 1000° C. to 1400° C.

9. A process according to claim 1, in which each row comprises at least one layer of heating means surrounded by sleeves which are substantially parallel to the reaction zone axis.

10. A process according to claim 1, applied to the production of acetylene, wherein said hydrocarbon containing at least one carbon atom comprises an acetylene precursor.

11. A process according to claim 1, applied to the production of methyl acetylene, wherein said hydrocarbon containing at least one carbon atom comprises a methyl acetylene precursor.

12. A pyrolysis and decoking unit for carrying out the process of claim 1, comprising a pyrolysis reactor (40) elongate in one direction (one axis) and comprising at least two rows (1, 2) which are substantially parallel to the axis and separated by a wall (70) of refractory material located between two successive rows, each row comprising a plurality of heating means (8) disposed in at least one layer of heating elements surrounded by sleeves (7) of ceramic material which are substantially parallel to each other and substantially perpendicular to the reactor axis, at least one of the rows being connected to a feed supply line (10) comprising at least one valve (VI) and to a steam supply line (60) comprising at least one valve (22), at least one other of said rows being connected to a supply line for a non hydrocarbon fluid containing steam for decoking and comprising at least one valve (21), said pyrolysis reactor comprising means for heat control and modulation connected to said heating means, the unit further comprising cooling means (47) for the effluents produced in each row, measuring means for the extent of decoking and switching means so as to permit pyrolysis to be continued in one row while decoking occurs in another row.

13. A process according to claim 1, in which the flow rate of the steam introduced into a decoking row is two to three times greater than the flow rate of steam introduced into a pyrolysis row.

14. A process according to claim 1, wherein said wall is non-impermeable, thereby permitting hydrogen to be transferred through the wall into a pyrolysis row so as to slow down deposition of coke therein.

15. A process according to claim 1, wherein said hydrocarbon containing at least one carbon atom is ethane.

16. A process according to claim 1, wherein said weight ratio of $H_2O$ to hydrocarbons is 0.65:1 to 10:1.

* * * * *